(12) United States Patent
Potin

(10) Patent No.: US 8,858,968 B2
(45) Date of Patent: Oct. 14, 2014

(54) USE OF TYROSINE-ARGININE DIPEPTIDE AND NIACINAMIDE AS SUBSTANCE P ANTAGONIST

(75) Inventor: Anthony Potin, Paris (FR)

(73) Assignee: L'Oreal, Paris (FR)

( * ) Notice: Subject to any disclaimer, the term of this patent is extended or adjusted under 35 U.S.C. 154(b) by 1218 days.

(21) Appl. No.: 11/566,708

(22) Filed: Dec. 5, 2006

(65) Prior Publication Data

US 2007/0154425 A1    Jul. 5, 2007

Related U.S. Application Data

(60) Provisional application No. 60/749,634, filed on Dec. 13, 2005.

(30) Foreign Application Priority Data

Dec. 5, 2005    (FR) ..................... 05 53729

(51) Int. Cl.
| | |
|---|---|
| A61K 8/64 | (2006.01) |
| A61K 8/49 | (2006.01) |
| A61Q 19/00 | (2006.01) |
| A61K 38/05 | (2006.01) |
| A61K 8/67 | (2006.01) |
| A61Q 7/00 | (2006.01) |

(52) U.S. Cl.
CPC ............ *A61K 8/675* (2013.01); *A61Q 19/005* (2013.01); *A61K 2800/75* (2013.01); *A61Q 19/00* (2013.01); *A61K 8/64* (2013.01); *A61K 38/05* (2013.01); *A61Q 7/00* (2013.01)
USPC .......................... 424/401; 424/62; 424/70.14

(58) Field of Classification Search
USPC .................................................. 424/401
See application file for complete search history.

(56) References Cited

U.S. PATENT DOCUMENTS

| | | | | |
|---|---|---|---|---|
| 5,827,886 | A | * | 10/1998 | Hersh ........................ 514/562 |
| 6,444,647 | B1 | | 9/2002 | Robinson et al. |
| 2004/0146539 | A1 | * | 7/2004 | Gupta ........................ 424/401 |
| 2005/0053572 | A1 | | 3/2005 | Hwang et al. |

FOREIGN PATENT DOCUMENTS

| | | |
|---|---|---|
| DE | 40 18 964 | 6/1990 |
| EP | 0 583 479 | 2/1994 |
| WO | WO 94/09750 | 5/1994 |
| WO | WO 98/07744 | 2/1998 |
| WO | WO 98/09985 | 3/1998 |
| WO | WO 00/02593 | 1/2000 |
| WO | WO 04/000333 | 12/2003 |
| WO | WO 2004/000333 | 12/2003 |
| WO | WO 2006/042625 | 4/2006 |
| WO | WO 2006/042626 | 4/2006 |

* cited by examiner

*Primary Examiner* — Audrea Buckley
(74) *Attorney, Agent, or Firm* — Oblon, Spivak, McClelland, Maier & Neustadt, L.L.P.

(57) ABSTRACT

Use of the combination of the tyrosine-arginine dipeptide or derivatives thereof and of niacinamide as a substance P antagonist for treating red blotches on the skin, skin oedema and sensitive skin. Use of this combination for the preparation of a composition for use in treating disorders associated with an excess synthesis and/or release of substance P.

31 Claims, No Drawings

USE OF TYROSINE-ARGININE DIPEPTIDE AND NIACINAMIDE AS SUBSTANCE P ANTAGONIST

REFERENCE TO PRIOR APPLICATIONS

This application claims priority to U.S. provisional application 60/749,634 filed Dec. 13, 2005, and to French patent application 0553729 filed Dec. 5, 2005, both incorporated herein by reference.

FIELD OF THE INVENTION

The technical field of the present invention is the treatment of the skin and/or of the mucous membranes and/or of the scalp.

In preferred embodiments the invention relates to the use of the combination of the tyrosine-arginine dipeptide, and/or derivatives thereof, and of niacinamide as a substance P antagonist, in particular for treating disorders associated with an excess synthesis and/or release of substance P.

The invention also relates to the use of the combination of the tyrosine-arginine dipeptide, and/or derivatives thereof, and of niacinamide for treating sensitive skin and also to cosmetic and dermatological treatment processes for sensitive skin.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

There exists, in mammals, polypeptides belonging to the tachykinin family that induce rapid contractions on smooth muscle fibres. Among the compounds of this family, mention may be made of neurokinin-β, neurokinin-α and substance P.

Substance P is a polypeptide (undecapeptide) chemical element produced and released by a nerve ending. The location of substance P is neurone-specific, both in the central nervous system and in peripheral organs. Thus, a very large number of organs or tissues receive substance P neuron afferences; they are, in particular, salivary glands, the stomach, the pancreas, the intestine (in the latter, the distribution of substance P is superimposed with Meissner's and Auerbach's intrinsic nerve plexuses), the cardiovascular system, the thyroid gland, the skin, the iris and the ciliary bodies, the bladder and, of course, the central and peripheral nervous systems.

By virtue of the ubiquitous distribution of substance P, numerous disorders are associated with an excess synthesis and/or release of substance P.

Substance P is in particular involved in the transmission of pain and in central nervous system diseases (for example, anxiety, psychoses, neuropathies, neurodegenerative conditions such as Alzheimer's senile dementia, age-related dementia, Parkinson's disease, Down's syndrome, Korsakoff's syndrome, multiple sclerosis, schizophrenia), in respiratory diseases (such as, for example, bronchial pneumonia) and inflammatory diseases (such as, for example, rheumatoid arthritis), in allergic syndromes (such as, for example, asthma, allergic rhinitis, allergic pharyngitis, urticaria, eczematous dermatitis), in gastrointestinal diseases (such as, for example, ulcers, colitis, Crohn's disease), in skin disorders (such as, for example, rosacea, psoriasis, pruriginous diseases, herpes, photodermatoses, atopic dermatitis, contact dermatitis, lichens, pruritis, prurigo, erythema, in particular solar erythema, insect bites), in fibroses and other conditions of collagen maturation (such as, for example, scleroderma), in cardiovascular conditions, vasospastic conditions (such as, for example, migraines, Reynaud's disease), in immunological disorders, in urinary tract conditions (such as, for example, incontinence, cystitis), in rheumatic diseases, in certain dermatological diseases (such as eczema) and in ophthalmological conditions (such as, for example, conjunctivitis, uveitis, ocular pruritis, ocular pain, irritations).

More specifically, when it is released in the skin, substance P exerts a vasodilatation and a plasma extravasation that can induce redness of the skin and oedema.

The use of a substance P antagonist is an effective means of preventing and/or reducing and/or treating the manifestations mentioned above.

The term "substance P antagonist" as used herein is intended to mean any compound capable of partially, or even totally, inhibiting the biological effect of substance P. In particular, for a substance to be recognized as a substance P antagonist, it must induce a coherent pharmacological response (possibly including its binding to the substance P receptor), for example in one of the following tests:
- the antagonist substance must decrease plasma extravasation through the vascular wall induced by capsaicin or by an antidromic nerve stimulation, or else
- the antagonist substance must cause an inhibition of the smooth muscle contraction induced by the administration of substance P.

It has also been demonstrated that substance P may be responsible for skin manifestations that characterize sensitive skin; the term "skin" is intended to mean any cutaneous surface of the body including the scalp.

In general, sensitive skin is defined by a specific reactivity of the skin. This skin reactivity is conventionally reflected by the manifestation of signs of discomfort in response to the individual coming into contact with a triggering element which may have various origins. It may be the application of a cosmetic product to the surface of the sensitive skin, the ingestion of food products, exposure to abrupt temperature variations, to atmospheric pollution and/or to ultraviolet or infrared rays. Related factors such as age and skin type also exist. Thus, sensitive skin is more common among dry or greasy skin than among normal skin.

The appearance of these signs of discomfort, which appear within minutes following the individual coming into contact with the triggering element, is one of the essential characteristics of sensitive skin. They involve mainly dysaesthesic sensations. The term "dysaesthesic sensations" is intended to mean more or less painful sensations felt in an area of skin, such as stinging, pins and needles, itching, burning, overheating, discomfort, tautness, etc. These subjective signs most commonly exist in the absence of visible clinical signs such as redness and desquamations. It is today known that these skin intolerance and irritation reactions are in particular related to a release of neuropeptides by the epidermal and dermal nerve endings.

In contrast with skin described as allergic, the reactivity of sensitive skin is not the result of an immunological process. Its response mechanism is termed "aspecific". It is, in this respect, to be distinguished from skin that shows inflammatory and allergic reactions of dermatosis, eczema and/or ichtyosis type, and with respect to which a certain number of treatments have already been proposed.

For obvious reasons, the absence of visible signs makes it difficult to diagnose sensitive skin. Most commonly, this diagnoses is based on questioning the patient. This symptomatology also has the advantage of making it possible to differentiate sensitive skin from contact irritation or allergy for which, on the other hand, visible inflammatory signs exist.

Consequently, the development of "sensitive skin" products has required the provision of tools for evaluating the sensorial reaction of the skin. The inspiration for the first tools, starting with their design, came from the essential characteristic of sensitive skin, namely the presence of signs of discomfort induced by a topical application.

Thus, the lactic acid "stinging test" was the first test proposed. It is carried out by recording stinging sensations reported by a volunteer after application of a 10% lactic acid solution to the sides of the nose. Individuals reporting moderate or strong stinging sensations are called "stingers" and are considered to have sensitive skin. Because of this sensitivity of the skin to the topical application of a product, these individuals are than selected for testing "sensitive skin" products. More recently, in order to specifically activate the peripheral nerve endings involved in discomfort, and called nociceptors, recently identified as being involved in sensitive skin, new tests have been proposed that in fact use other inducers of discomfort such as capsaicin.

This second type of test, described in application EP 1 374 913, also constitutes another particularly useful means for the diagnosis of sensitive skin.

For the purpose of the present invention, sensitive skin can cover irritable skin and intolerant skin. Intolerant skin is skin that reacts to various factors, such as the application of cosmetic or dermatological products or soap, through sensations of overheating, tautness, pins and needles and/or redness. In general, these signs are associated with erythema and with hyperseborrheic or acneic skin, or even skin exhibiting rosacea, with or without sores. lrritable skin is skin that reacts through pruritus, i.e. through itching or stinging, to various factors such as the environment, emotions, foods, the wind, rubbing, shaving, hard water with a high calcium concentration, temperature variations, humidity or wool.

"Sensitive" scalps have a more unambiguous clinical semiology: the itching and/or stinging and/or overheating sensations are essentially triggered by local factors such as rubbing, soap, surfactants, hard water with a high calcium concentration, shampoos or lotions. These sensations are also sometimes triggered by factors such as the environment, emotions and/or foods. An erythema and hyperseborrhae of the scalp and also dandruff are frequently associated with the above signs.

SUMMARY OF THE INVENTION

The inventor has demonstrated that the combination of the tyrosine-arginine dipeptide, and/or derivatives thereof, and of niacinamide exhibits a significantly improved activity as a substance P antagonist, compared to the activity of each of these active agents taken separately. That is, there is a synergistic result when these materials are used in combination. It is therefore advantageous to use this combination of niacinamide and dipeptide for the treatment of disorders related to an excessive release of substance P.

DETAILED DESCRIPTION OF THE PREFERRED EMBODIMENTS

A subject of the invention is thus the combination itself, as well as its use, each prefereably in a cosmetic or dermatological or pharmaceutical composition, of an effective amount of the tyrosine-arginine dipeptide, and/or derivatives thereof, and of niacinamide as a substance P antagonist.

The tyrosine-arginine dipeptide is known for its analgesic and calmative properties (WO 98/07744); it has also been described as a muscle relaxant.

The dipeptide corresponds to the following general formula: R1-L-Tyr-L-Arg-R2 with R1 is a hydrogen atom or an —R3-C=O group and R3 is an optionally hydroxylated, saturated or unsaturated, linear or branched alkyl chain containing from 1 to 20 carbon atoms, or an aryl group, an arylalkyl group, an alkyloxy group or an arylalkyloxy group, and R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

It may be that, for reasons of resistance to degradation, it is advantageous to use a protected form of the peptide. The form of the protection should be a biologically compatible form. Numerous biologically compatible protection forms are included, for instance acylation or acetylation of the amino-terminal end or amidation of the carboxy-terminal end.

Preferably, the N-acetyl-tyrosine-arginine-O-hexadecyl ester that has advantageous lipophilicity, stability and bio-availability properties is used.

The synthesis of the dipeptide and of modified forms thereof is described in WO 98/07744.

The term "dipeptide" or "tyrosine-arginine dipeptide" or "tyr-arg dipeptide" will subsequently be used without distinction to denote the tyrosine-arginine dipeptide and optionally modified derivatives thereof, with the proviso of exhibiting an equivalent biological activity.

Niacinamide, also called nicotinic acid, nicotinamide or alternatively vitamin B3, is pyridine-3-carboxamide, a member of the family of 8 water-soluble B vitamins. Vitamin B3 is necessary for cellular respiration, for aiding energy metabolism and carbohydrate, lipid and protein metabolism, and for blood circulation. This vitamin is also known to exhibit anti-inflammatory properties.

The symptoms of a vitamin B3 deficiency comprise indigestion, fatigue, and even vomiting and depression.

More particularly, the combination of niacinamide and tyrosine-arginine dipeptide, and/or derivatives thereof, can be used for example to embellish the appearance of the skin and/or the mucous membranes, preventing and/or reducing the intensity of red blotches on the skin and/or slight skin oedema, lightening and/or making uniform the complexion and/or masking surface red blotches and/or fading out the signs of skin microcirculation, i.e. making less visible the blood capillaries that are noticeable, in particular on the face.

The combination of niacinamide and dipeptide and/or derivatives thereof may also be used for preventing a puffy appearance of the skin caused by slight oedema and, for example, may be formulated in care products for making the figure, the neck and/or the oval of the face more slender, decreasing bags under the eyes, treating puffy ankles and legs, etc.

An excess of substance P in the scalp can also lead to capillary disorders and/or result in a modification of the colour of the hair follicles, or a modification of the density, the quantity or the quality of the hair, as a consequence, for example, of a slowing down or an arrest of the growth of hair follicles, of a loss of hair follicles or of an exacerbated growth of hair follicles.

Thus, another use of the combination of niacinamide and dipeptide and/or derivatives thereof relates to hair treatment compositions (shampoo, lotion, masks, etc.) for limiting and/or preventing hair loss and thus treating alopecia of any nature whatsoever and/or promoting the growth of healthy hair.

The use of the combination of niacinamide and tyrosine-arginine dipeptide and/or derivatives thereof may also be intended for the treatment of sensitive skin, in particular intolerant or irritable skin, for preventing and/or decreasing dysaesthesic sensations, for preventing and/or decreasing stinging and/or pins and needles and/or itching and/or overheating and/or skin discomfort and/or tautness of the skin.

Another subject of the present invention relates to the use of an effective amount of niacinamide and of the tyrosine-arginine dipeptide and/or derivatives thereof, for the preparation of a composition for use in treating disorders associated with an excess synthesis and/or release of substance P, in particular skin disorders.

The disorders associated with an excess synthesis and/or release of substance P are as described above.

According to a preferred aspect of the invention, an effective amount of niacinamide and of the tyrosine-arginine dipeptide and/or derivatives thereof is used for the preparation of a composition for use in treating skin disorders, in particular chosen from urticaria, eczematous dermatitis, rosacea, psoriasis, herpes, photodermatoses, atopic dermatitis, contact dermatitis, lichen, prurigos, pruriginous diseases, fibroses, collagen maturation conditions, scleroderma and eczema.

The combination of niacinamide and of tyrosine-arginine dipeptide and/or derivatives thereof is particularly suitable for treating the signs of rosacea, in particular the first stage thereof.

Rosacea is a common, chronic and progressive dermatosis related to vascular relaxation. It mainly affects the central part of the face and is characterized by redness of the face or hot flushes, facial erythema, papules, pustules and telangiectasia. In serious cases, especially in men, the soft tissue of the nose may swell and produce a bulbous swelling known as rhinophyma.

Rosacea generally develops in 4 stages:
  stage 1 of vascular relaxation (at about 20 years old). The patients experience sudden bursts of paroxystic redness of the face and neck, with a hot sensation, but with no systemic signs. After the attacks, the skin of the face returns to normal. These "flushes" are triggered by changes in temperature (occasionally leading to thermophobia), and the intake of hot drinks or alcohol;
  stage 2 of erythemato-telangiectasia (at about 30 years old). The cheekbone areas are diffusively red. Dilated capillaries constituting standard acne rosacea are observed therein. In contrast with stage 1, the redness is permanent. Besides the cheeks, the chin and the middle of the forehead may be effected;
  stage 3 of papulo-pustules (at about 40 years old). Papules and pustules a few millimetres in diameter develop on a background of erythema, without associated comedones. This dermatosis may be very extensive, occasionally up to the ball part of the scalp in men, but is absent from the area around the mouth and the eyes. The patients complain of sensitive skin, with subjective intolerance to the majority of topical products and greasy cosmetics;
  stage 4 of rhinophyma (at about 50 years old or later). This late phase mainly affects men, in contrast with the other stages. The nose is increased in volume and diffusely red and the follicular orifices are dilated. The skin gradually thickens.

A subject of the present invention is also a cosmetic treatment process, characterized in that an effective amount of the combination of tyrosine-arginine dipeptide and/or derivatives thereof and niacinamide is applied to the skin, to the scalp and/or to the mucous membranes of the cutaneous areas.

In particular, it may be a cosmetic process for preventing and/or fading out red blotches and/or signs of skin microcirculation and/or skin oedema and/or limiting and/or preventing hair loss and/or promoting the growth of healthy hair, characterized in that an effective amount of the combination of niacinamide and tyrosine-arginine dipeptide or derivatives thereof is applied to the skin, to the scalp and/or to the mucous membranes.

The present invention also relates to a cosmetic treatment process for sensitive skin, characterized in that an effective amount of the combination of niacinamide and tyrosine-arginine dipeptide and/or derivatives thereof is applied to the skin, to the scalp and/or to the mucous membranes.

A description of what is meant by irritable skin was given above. The skin irritation may have many causes. They may be intrinsic causes, related to the disregulation of the physiological mechanisms that produce normal skin. However, there may also be extrinsic causes, such as irritant compounds that come into contact with the skin.

Thus, a subject of the present invention is also a cosmetic process for the purpose of decreasing skin irritation, characterized in that the combination of niacinamide and of dipeptide and/or derivatives thereof is used by application to the skin, to the hair and/or to the mucous membranes.

The cosmetic processes of the invention can be carried out in particular by applying the hygiene or cosmetic compositions as defined above, according to the normal technique for using these compositions. For example: application of creams, gels, sera, lotions, sticks, make-up removing milks or antisun compositions to the skin or to dry hair, application of a hair lotion to wet hair, of shampoos, or alternatively application of toothpaste to the gums.

The effective amounts of niacinamide and of dipeptide and/or derivatives thereof correspond to the required amount of each of the two compounds for exhibiting an improved effect.

The tests carried out in the context of the present invention (see Examples 1 and 2) have made it possible to demonstrate, surprisingly, that the combination of niacinamide and dipeptide produces a substance P antagonist activity that is much greater than the activity of these active agents taken separately.

Preferably, in the compositions according to the invention, a physiologically acceptable medium is present, and the dipeptide and/or derivatives thereof is/are present in concentrations of between 0.001% and 20%, preferably between 0.01% and 10%, and the niacinamide is present in concentrations of between 0.01% and 20%, preferably between 0.1% and 10%.

Advantageously, the composition according to the invention will also comprise at least one calmative. As examples of "calmatives" that can be used in the compositions of the invention, included are:
  beta-glycyrrhetinic acid, the extracts containing same, for example extract of *Glycyrrhiza glabra* (liquorice), and the complexes containing same, such as the allantoin/glycyrrhetinic acid complex;
  planktons, which may or may not be lyophilized, extracts thereof and complexes thereof;
  escin and the plant extracts containing same, such as extract of horse chestnut;

xanthin derivatives, such as diethylaminoethyltheophylline hydrochloride and caffeine;

waters and extracts (for example, aqueous, aqueous-alcoholic or water-glycol extracts) of flowers or plants, such as corn flour water, camomile water, mint water, lime blossom water or rose water, extracts of Rosacea plants (for example, *Rosa gallica*), extracts of peony, extracts of hawthorn, extracts of yarrow, extracts of mallow, extracts of marigold, extracts of melilot, extracts of sage, extracts of elder, extracts of ginkgo biloba, extracts of arnica, extracts of oregano, extracts of green tea, extracts of waterlily blossom, extracts of iris, extracts of birch bark and extracts of aloe vera;

Asiatic acid and plant extracts containing same, such as *Centella asiatica*;

fruit extracts, such as extract of pineapple, extract of papaya; extract of guava;

algae, in particular of the *Laminaria* type, (for example, red or brown algae);

pyrrolidonecarboxylates, and in particular of zinc (Zn-PCA) or of copper (Cu-PCA);

oils of plant origin, such as canola seed oil and shear butter;

essential oils, for example of coriander, of balm, of lavender, of mint or of camomile, and mixtures thereof;

acexamic acid and transexamic acid (trans-4-aminomethylcyclohexanecarboxylic acid);

ursolic acid and extracts containing same, such as extract of rosemary leaf;

polysaccharides containing fucose, such as FUCOGEL 1000, sold by Solabia (aqueous solution containing 1% polysaccharide solids comprising fucose, galactose and galacturonic acid);

electrolytes, and in particular an aqueous mixture comprising from 30% to 35% of magnesium chloride, from 20% to 28% of potassium chloride, from 3% to 10% of sodium chloride, from 0.2% to 1% of calcium chloride, from 0.1% to 0.6% of magnesium bromide and from 0.1% to 0.5% of insoluble matter, said mixture being referred to herein as "Dead Sea Bath Salts" since it corresponds to the main salts contained in the Dead Sea;

galactolipids derived, for example, from oat, for instance digalactosyl diglyceride or monogalactosyl diglyceride;

amino acids, derivatives thereof and salts thereof, such as the sodium salt of amino acids grafted onto cocoyl chains, sold in the form of a mixture under the name SEPICALM S by the company SEPPIC, capryloylglycine sold under the name LIPACIDE C8G by the company SEPPIC, and the mixture of capryloylglycine, cinnamon and sarcosine sold under the name SEPICONTROL A5 by the company SEPPIC;

TNF-alpha antagonists, such as lisophylline I'A802715, sulfasalazine, CDP-571 (anti-TNF-alpha antibody) or MDL-201112;

substance P antagonists, such as sendide, spantide II, and the peptides described in application EP-A-680749, and the extracts of filamentous bacteria described in application EP-A-761204;

CGRP antagonists, such as CGRP 8-37, anti-CGRP antibodies, or plant extracts with CGRP antagonist activity (for example: *Iris pallida*);

divalent strontium, zinc, manganese, magnesium and calcium salts, such as those described in documents WO-A-96/19184, WO-A-96/19182 and WO-A-96/19228;

and mixtures thereof.

Preferably, the calmative may be chosen from extracts of rose, bisabolol, D-panthenol, allantoin, madecassoside, extracts of *Centella asiatica*, potassium glycyrrhizinate or caffeine.

The amount of calmative(s) may range, for example, from 0.001% to 20% by weight, and preferably from 0.01% to 15% by weight, relative to the total weight of the composition.

According to the desired purpose of the composition according to the invention, it may also comprise active agents that will be chosen such that they do not harm the effect of the combination of niacinamide and dipeptide and/or derivatives thereof.

Among these active agents, included are:

Desquamating Agents and Moisturizers:

The term "desquamating agent" is intended to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Saphora japonica*; resveratrol and certain jasmonic acid derivatives;

or on the enzymes involved in desquamation or the degradation of corneodesmosomes, glycosidases, stratum corneum chymotryptic enzyme (SCCE), or even other proteases (trypsin, chymotrypsin-like). Mention may be made of agents for chelating mineral salts: EDTA; N-acyl-N,N',N'-ethylenediaminetriacetic acid; aminosulfonic compounds and in particular (N-2-hydroxyethylpiperazine-N-2-ethane)sulfonic acid (HEPES); 2-oxothiazolidine-4-carboxylic acid (procysteine) derivatives; derivatives of alpha-amino acids of glycine type (as described in EP-O 852 949, and also sodium methylglycinediacetate sold by BASF under the trade name TRILON M); honey; sugar derivatives such as O-octanoyl-6-D-maltose and N-acetylglucosamine.

The term "moisturizer" is intended to mean:

either a compound that acts on the barrier function, with a view to maintaining the moisturization of the stratum corneum, or an occlusive compound. Mention may be made of ceramides, sphingoid-based compounds, lecithins, glycosphingolipids, phospholipids, cholesterol and its derivatives, phytosterols (stigmasterol, β-sitosterol, campesterol), essential fafty acids, 1-2 diacylglycerol, 4-chromanone, pentacyclic triterpenes such as ursolic acid, petroleum jelly and lanoline;

or a compound that directly increases the water content of the stratum corneum, such as threalose and its derivatives, hyaluronic acid and its derivatives, glycerol, pentanediol, sodium pidolate, serine, xylitol, sodium lactate, poly(glyceryl acrylate), ectoin and its derivatives, chitosan, oligosaccharides and polysaccharides, cyclic carbonates, N-lauroylpyrrolidonecarboxylic acid, and N-α-benzoyl-L-arginine;

or a compound that activates sebaceous glands, such as steroidal derivatives (including DHEA, its 7-oxidized and/or 17-alkylated derivatives, and sapogenins), methyl dihydrojasmonate, and vitamin D and its derivatives.

These compounds may represent from 0.001% to 30%, and preferably from 0.01% to 20%, of the total weight of the composition according to the invention. The composition according to the present invention comprising the desquamating agents and moisturizers mentioned above is advantageously for use in the prevention or treatment of drying out of the skin, and in particular of xerosis.

Depigmenting, Anti-pigmenting or Pro-pigmenting Agents:

The depigmenting or anti-pigmenting agents that may be incorporated into the composition according to the present invention comprise, for example, the following compounds: kojic acid; ellagic acid; arbutin and its derivatives, such as those described in applications EP-895 779 and EP-524 109; hydroquinone; aminophenol derivatives such as those described in applications WO 99/10318 and WO 99/32077, and in particular N-cholesteryloxycarbonyl-para-aminophenol and N-ethyloxycarbonyl-para-aminophenol; iminophenol derivatives, in particular those described in application WO 99/22707; L-2-oxothiazolidine-4-carboxylic acid or procysteine, and its salts and esters; calcium D-pantetheine sulfonate, and ascorbic acid and its derivatives; in particular ascorbyl glucoside; plant extracts, in particular extracts of liquorice, of mulberry, of skullcap and of *Bacopa monnieri*, without this list being limiting.

As pro-pigmenting agents, mention may be made of the extract of pimpernel (*Sanguisorba officinalis*) sold by MARUZEN and extracts of chrysanthemum (*Chrysanthemum morifolium*).

Anti-qlycation Agents:

The term "anti-glycation agent" is intended to mean a compound for preventing and/or decreasing the glycation of skin proteins, in particular of dermal proteins such as collagen.

Examples of anti-glycation agents are extracts of plants of the Ericaceae family, such as an extract of blueberry (*Vaccinium angusffifolium*); ergothioneine and its derivatives; and hydroxystilbenes and their derivatives, such as resveratrol and 3,3', 5,5'-tetrahydroxystilbene. These anti-glycation agents are described in applications FR 2 802 425, FR 2 810 548, FR 2 796 278 and FR 2 802 420, respectively. Resveratrol is particularly preferred for use in this invention.

The composition according to the invention comprising an anti-glycation agent as defined above can advantageously be used for preventing or treating the signs of skin ageing, in particular for preventing or treating the loss of tonicity and/or of elasticity of the skin.

NO-synthase Inhibitors:

Examples of NO-synthase inhibitors that are suitable for use in the present invention comprise, in particular, an extract of a plant of the species *Vitis vinifera* which is in particular sold by Euromed under the name "Leucocyanidines de raisins extra", or alternatively by Indena under the name "Leucoselect®" or, finally, by Hansen under the name "Extrait de marc de raisin"; an extract of a plant of the species *Olea europaea* which is preferably obtained from olive tree leaves and is in particular sold by VINYALS in the form of a dry extract, or by Biologia & Technologia under the trade name Eurol BT; and an extract of a plant of the species *Gingko biloba* which is preferably a dry aqueous extract of this plant sold by Beaufour under the trade name "*Ginkgo biloba* extrait standard".

The composition according to the invention comprising an NO-synthase inhibitor as defined above can advantageously be used for preventing or treating the signs of skin ageing and/or sensitive skin.

Anti-seborrheic Agents:

When the composition according to the invention comprises an anti-seborrheic agent such as a 5α-reductase inhibitor, said agent can in particular be chosen from:

retinoids, and in particular retinol;
sulphur and sulphur derivatives;
zinc salts such as zinc lactate, zinc gluconate, zinc pidolate, zinc carboxylate, zinc salicylate and/or zinc cysteate;
selenium chloride;
vitamin B6 or pyridoxine;
the mixture of capryloyl glycine, sarcosine and extract of *Cinnamomum zeylanicum* sold in particular by SEPPIC under the trade name Sepicontrol A5®;
an extract of *Laminaria saccharina* sold in particular by SECMA under the trade name Phlorogine®;
an extract of *Spiraea ulmaria* sold in particular by SILAB under the trade name Sebonormine®;
extracts of plants of the species *Arnica montana*, *Cinchona succirubra*, *Eugenia caryophyllata*, *Humulus lupulus*, *Hypericum perforatum*, *Mentha piperita*, *Rosmarinus officinalis*, *Salvia officinalis* and *Thymus vulgaris* all sold, for example, by MARUZEN;
an extract of *Serenoa repens* sold in particular by EUROMED;
extracts of plants of the genus *Silybum*; and
extracts of *Eugenia caryophyllata* containing eugenol and eugenyl glucoside.

The 5α-reductase inhibitor represents, for example, from 0.001% to 10%, and preferably from 0.01% to 5%, of the total weight of the composition according to the invention, When the latter contains such a compound, it is particularly suitable for preventing or treating seborrhoea and/or hirsutism and/or androgen-dependent alopecia.

Inhibitors of Lysyl and/or Propyl Hydroxylase:

Preferred examples of inhibitors of lysyl and/or propyl hydroxylase that can be used in the composition according to the present invention are 2,4-diaminopyrimidine 3-oxide or 2,4-DPO described in patent application WO 96/09048 and 2,4-diamino-6-piperidinopyrimidine 3-oxide or "Minoxidil" described in U.S. Pat. No. 4,139,619 and U.S. Pat. No. 4,596, 812.

These compounds are, for example, present in the composition according to the invention in an amount of from 0.001% to 5% by weight, and better still in an amount of from 0.01% to 5% by weight, relative to the total weight of the composition.

The composition containing the inhibitor of lysyl and/or propyl hydroxylase and the DHEA derivative according to the invention is advantageously used for the prevention or treatment of alopecia.

Agents for Stimulating the Synthesis of Dermal or Epidermal Macromolecules and/or for Preventing their Degradation:

Among the active agents for stimulating dermal macromolecules or for preventing their degradation, mention may be made of those that act:

either on collagen synthesis, such as extracts of *Centella asiatica*; asiaticosides and derivatives, ascorbic acid or vitamin C and its derivatives; synthetic peptides such as iamin, biopeptide CL or palmitoyloligopeptide sold by SEDERMA; peptides extracted from plants, such as the soybean hydrolysate sold by COLETICA under the trade name Phytokine®; and plant hormones such as auxins and lignans;
or on elastin synthesis, such as the extract of *Saccharomyces cerivisiae* sold by LSN under the trade name Cytovitin®; and the extract of the alga *Macrocystis pyrifera* sold by SECMA under the trade name Kelpadelie®;
or on glycosaminoglycan synthesis, such as the product of fermentation of milk with *Lactobacillus vulgaris*, sold by the company BROOKS under the trade name Biomin yogourth®; the extract of the brown alga *Padina pavonica* sold by ALBAN MÜLLER under the trade name HSP3®; and the extract of *Saccharomyces cerevisiae* available in particular from SILAB under the trade name Firmalift® or from LSN under the trade name Cytovitin®;

or on fibronectin synthesis, such as the extract of the zooplankton *Salina* sold by SEPORGA under the trade name GP4G®;

the yeast extract available in particular from ALBAN MÜLLER under the trade name Drieline®; and the palmitoyl pentapeptide sold by SEDERMA under the trade name Matrixil®;

or on the inhibition of metalloproteinases (MMP) such as, more particularly, MMP 1, 2, 3 or 9. Mention may be made of: retinoids and derivatives, oligopeptides and lipopeptides, lipoamino acids, the malt extract sold by COLETICA under the trade name Collalift®; extracts of blueberry or of rosemary; lycopene; isoflavones, their derivatives or plant extracts containing them, in particular extracts of soybean (sold, for example, by ICHIMARU PHARCOS under the trade name Flavostérone SB®), of red clover, of flax, of kakkon or of sage;

or on the inhibition of serine proteases such as leukocyte elastase or cathepsin G. Mention may be made of: the peptide extract of *Leguminosa* seeds (*Pisum sativum*) sold by LSN under the trade name Parelastyl®; heparinoids; and pseudodipeptides such as {2-[acetyl-(3-trifluoromethylphenyl)amino]-3-methylbutyrylamino}acetic acid.

Among the active agents for stimulating epidermal macromolecules, such as fillagrin, and keratins, mention may in particular be made of the extract of lupin sold by SILAB under the trade name Structurine®; the extract of *Fagus sylvatica* beech buds sold by GATTEFOSSE under the trade name Gatuline®; and the extract of the zooplankton *Salina* sold by SEPORGA under the trade name GP4G®.

The composition according to the invention containing one or more of the above compounds is particularly suitable for use in the prevention or treatment of the signs of skin ageing, in particular of the loss of firmness and/or elasticity of the skin.

Agents for Stimulating Fibroblast or Keratinocyte Proliferation and/or Keratinocvte Differentiation:

The agents for stimulating fibroblast proliferation that can be used in the composition according to the invention may, for example, be chosen from plant proteins or polypeptides, extracted in particular from soybean (for example, an extract of soybean sold by LSN under the name Eleseryl SH-VEG 8® or sold by SILAB under the trade name Raffermine®); and plant hormones such as giberrellins and cytokinins.

The agents for stimulating keratinocyte proliferation that can be used in the composition according to the invention comprise in particular retinoids such as retinol and its esters, including retinyl palmitate; adenosine; phloroglucinol; the extracts of walnut cakes sold by GATTEFOSSE; and the extracts of *Solanum tuberosum* sold by SEDERMA.

The agents for stimulating keratinocyte differentiation comprise, for example, minerals such as calcium; a peptide extract of a lupin such as that sold by SILAB under the trade name Structurine®; sodium beta-sitosteryl sulphate such as that sold by SEPORGA under the trade name Phytocohésine®; and a water-soluble extract of maize such as that sold by SOLABIA under the trade name Phytovityl®; a peptide extract of *Voandzeia substerranea* such as that sold by the Laboratoires Sérobiologiques under the trade name Filladyn LS 9397®; and lignans such as secoisolariciresinol.

The composition according to the invention comprising these compounds is preferably intended to be used for preventing or treating the signs of skin ageing.

Muscle Relaxants or Dermo-decontracting Agents:

The muscle relaxants or dermo-decontracting agents that can be used in the composition according to the invention comprise alverine and its salts, manganese gluconate, Diazepam, Argireline hexapeptide R sold by LIPOTEC, certain secondary and tertiary carbonyl amines, adenosine, and also sapogenins and natural extracts, in particular of Wild Yam, containing them, and also extracts of *Boswellia serrata*.

The composition according to the invention comprising these compounds is preferably intended to be used for preventing or treating the signs of skin ageing, and in particular wrinkles.

Anti-microbial Agents:

The antimicrobial agents that can be used in the composition according to the invention may in particular be chosen from 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerine, octanoylglycine, caprylyl glycol, 10-hydroxy-2-decanoic acid, dichlorophenylimidazole dioxolane and its derivatives described in patent WO 93/18743, farnesol and phytosphingosines, and mixtures thereof.

The preferred antimicrobial agents are triclosan, phenoxyethanol, octoxyglycerine, octanoylglycine, 10-hydroxy-2-decanoic acid, caprylyl glycol, farnesol and azelaic acid.

By way of example, the antimicrobial agent may be used in the composition according to the invention in an amount representing from 0.1% to 20%, and preferably from 0.1% to 10%, of the total weight of the composition.

The composition containing the antimicrobial agent is particularly suitable for use in the treatment of greasy skin with a tendency to be acneic, acne, or dandruff of the scalp.

Tensioning Agents:

The term "tensioning agent" is intended to mean a compound capable of exerting tension on the skin, the effect of which is to temporarily fade out irregularities on the skin's surface, such as wrinkles and fine lines.

Among the tensioning agents that can be used in the composition according to the present invention, mention may in particular be made of:

(1) synthetic polymers, such as polyurethane latices or acrylic-silicone latices, in particular those described in patent application EP-1038519, such as a propylthio(polymethyl acrylate), propylthio(polymethyl methacrylate) and propylthio(polymethacrylic acid) grafted polydimethylsiloxane, or alternatively a propylthio(polyisobutyl methacrylate) and propylthio(polymethacrylic acid) grafted polydimethylsiloxane. Such grafted silicone polymers are in particular sold by 3M under the trade names VS 80, VS 70 or LO21;

(2) polymers of natural origin, in particular (a) polyholosides, for example (i) in the form of starch derived in particular from rice, maize, potato, cassava, pea, *Triticum aestivum* wheat, oat, etc, or (ii) in the form of carraghenanes, alginates, agars, gelans, cellulose-based polymers and pectines, advantageously as an aqueous dispersion of gel microparticles, and (b) latices consisting of shellac resin, sandarac gum, dammar resins, elemi gums, copal resins and cellulose-based derivatives, and mixtures thereof;

(3) plant proteins and hydrolysates, in particular from maize, rye, *Triticum aestivum* wheat, buckwheat, sesame, spelt, pea, bean, lentil, soybean and lupin, (3) mixed silicates, especially phyllosilicates, and in particular Laponites, (4) wax microparticles chosen, for example, from Carnauba wax, Candelila wax and Alfa wax;

(5) colloidal particles of inorganic filler with a number-average diameter of between 0.1 and 100 nm, preferably between 3 and 30 nm, and chosen, for example, from: silica, silica-alumina composites, cerium oxide, zirconium oxide, alumina, calcium carbonate, barium sulphate, calcium sulphate, zinc oxide and titanium dioxide.

The compositions according to the invention comprising the tensioning agents above are advantageously for use in the treatment of the signs of skin ageing, in particular of wrinkles and fine lines.

Anti-pollution Agents or Free-radical Scavengers:

The term "anti-pollution agent" is intended to mean any compound capable of trapping ozone, monocyclic or polycyclic aromatic compounds such as benzopyrene and/or heavy metals such as cobalt, mercury, cadmium and/or nickel. The term "free-radical scavenger" is intended to mean any compound capable of trapping free radicals.

As ozone-trapping agents that can be used in the composition according to the invention, mention may in particular be made of vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chorogenic acid; stilbenes, in particular resveratrol; sulphur-containing amino acid derivatives, in particular S-carboxymethylcysteine; ergothioneine; N-acetylcysteine; chelating agents such as N,N'-bis(3,4,5-trimethoxybenzyl)ethylenediamine or one of its salts, metal complexes or esters; carotenoids such as crocetin; and various starting materials, such as the mixture of arginine, histidine ribonucleate, mannitol, adenosine triphosphate, pyridoxine, phenylalanine, tyrosine and hydrolyzed RNA, sold by the Laboratoires Sérobiologiques under the trade name CPP LS 2633-12F®, the water-soluble fraction of maize sold by SOLABIA under the trade name Phytovityl®, the mixture of extract of fumitory and of extract of lemon sold under the name Unicotrozon C-49® by Induchem, and the mixture of extracts of ginseng, of apple, of peach, of wheat and of barley, sold by PROVITAL under the trade name Pronalen Bioprotect®.

As agents for trapping monocyclic or polycyclic aromatic compounds that can be used in the composition according to the invention, mention may in particular be made of tannins such as ellagic acid; indole derivatives, in particular 3-indolecarbinol; extracts of tea, in particular of green tea, extracts of water hyacinth or *Eichhornia crassipes*; and the water-soluble fraction of maize sold by SOLABIA under the trade name Phytovityl®.

Finally, as heavy-metal-trapping agents that can be used in the composition according to the invention, mention may in particular be made of chelating agents such as EDTA, the pentasodium salt of ethylenediaminetetramethylenephosphonic acid, and N,N'-bis(3,4,5-trimethoxybenzyl) ethylenediamine or one of its salts, metal complexes or esters; phytic acid; chitosan derivatives; extracts of tea, in particular of green tea; tannins such as ellagic acid; sulphur-containing amino acids such as cysteine; extracts of water hyacinth (*Eichhornia crassipes*); and the water-soluble fraction of maize sold by SOLABIA under the trade name Phytovityl®.

The free-radical scavengers that can be used in the composition according to the invention comprise, in addition to certain anti-pollution agents mentioned above, vitamin E and its derivatives such as tocopheryl acetate; bioflavonoids; coenzyme Q10 or ubiquinone; certain enzymes such as catalase, superoxide dismutase and extracts of wheat germ containing same, lactoperoxidase, glutathione peroxidase and quinone reductases; glutathione; benzylidenecamphor; benzylcyclanones; substituted naphthalenones; pidolates; phytantriol; gamma-oryzanol; guanosine; lignans; and melatonin.

Lipolytic Active Agents or Active Agents Having a Direct or Indirect, Favourable Activity with Respect to Decreasing Adipose Tissue:

Among the derivatives capable of promoting lipolysis, the following may be found:

1) phosphodiesterase inhibitors, such as:
    xanthine derivatives such as caffeine and its derivatives, in particular the 1-hydroxyalkylxanthines described in document FR-A-2,617,401, caffeine citrate, theophylline and its derivatives, theobromine, acefylline, aminophylline, chloroethyltheophylline, diprofylline, diniprophylline, etamiphylline and its derivatives, etofylline and proxyphylline;
    combinations containing xanthine derivatives, such as the combination of caffeine and silanol (caffeine methyl silanetriol derivative), and, for example, the product sold by Exsymol under the name "caféisilane C";
    compounds of natural origin containing xanthine bases, and in particular caffeine, such as extracts of tea, of coffee, of guarana, of maté, of cola (*Cola nitida*) and in particular the dry extract of guarana fruit (*Paulina sorbilis*) containing 8% to 10% of caffeine;
    ephedrine and its derivatives that can in particular be found in natural form in plants such as Ma Huang (Ephedra plant);

2) plant extracts and extracts of marine origin, which either are active on the receptors to be inhibited, such as β-2-blockers or NPY blockers (described in patent EP 838217), or which inhibit the synthesis of LDL or VLDL receptors, or which are active in stimulating β-receptors and G proteins, resulting in the activation of adenylcyclase. As plant extracts of this type, mention may, for example, be made of:

*Garcinia cambogia*,
    extracts of *Bupleurum chinensis*,
    extracts of English ivy (*Hedera helix*), of arnica (*Arnica montana L*), of rosemary (*Rosmarinus officinalis L*), of marigold (*Calendula officinalis*), of sage (*Salvia officinalis L*), of ginseng (*Panax ginseng*), of St John's wart (*Hyperycum perforatum*), of butcher's broom (*Ruscus aculeatus L*), of meadowsweet (*Filipendula ulmaria L*), of cat's whiskers (*Orthosiphon staminus benth*), of birch (*Betula alba*), of cecropia and the argania tree,
    extracts of ginkgo biloba,
    extracts of horsetail,
    extracts of escin,
    extracts of cangzhu,
    extracts of *Chrysanthellum indicum*,
    extracts of diosscorea rich in diosgenin or pure diosgenin or hecogenin and derivatives thereof,
    extracts of plants of the genus *Armeniacea, Atractylodis Platicodon, Sinommenum, Pharbitidis, Flemingia*, extracts of *Coleus* such as *C. forskohlii, C. blumei, C. esquirolii, C. scutellaroides, C. xanthantus* and *C. barbatus*, such as the extract of *Coleus barbatus* root containing 60% forskolin, extracts of ballota, extracts of *Guioa*, of *Davallia*, of *Terminalia*, of *Barringtonia*, of *Trema* and of *Antirobia*.

As extracts of marine origin, mention may be made of alga or phytoplankton extracts, such as rhodysterol or the extract of *Laminaria digitata* sold under the name PHYCOX75 by Secma, the alga skeletonema described in patent FR 2 782 921 or the diatomeae described in patent FR 2774292;

3) Peptides or proteins

Peptides derived from parathyroid hormone, as described in patents FR 2 788058 and FR 2 781231 from Sederma, or the peptides described in document FR 2 786 693, or even any another peptide having lipolytic properties, protamines and their derivatives such as those described in document FR-A-2,758,724.

The amount of lipolytic active agent(s) can vary to a large extent and depends on the nature of the active agent(s) used. In general, the slimming active agent(s) is (are) present at a concentration ranging from 0.001% to 20%, and preferably from 0.1% to 10%, by weight relative to the total weight of the composition.

Agents that Act on the Microcirculation:

The agents that act on the microcirculation (vasoprotector or vasodilatator) can be chosen from flavonois, ruscogenins, esculosides, escin extracted from horse chestnut, nicotinates, heperidine methyl chalcone, essential oils of lavender or of rosemary, and extracts of *Ammi visnaga*.

The amount of these active agents can vary to a large extent. In general, these active agents are present at a concentration ranging from 0.01% to 15%, and preferably from 0.05% to 10%, by weight relative to the total weight of the composition.

And Agents that Act on the Energy Metabolism of Cells:

The active agents concerned are those that act on cutaneous energy metabolism, for instance, and in a nonlimiting manner, ATP synthesis, and those which intervene on the respiratory chain of the cell or on the energy stores. Mention may be made of coenzyme Q10 (ubiquinone), cytochrome C, creatine or else phosphocreatine.

Topical compounds whose use may, under specific circumstances such as reactive skin, skin suffering from rosacea, high concentrations of said compounds, etc., result in the appearance of red blotches on the skin are used in cosmetic or dermatological compositions, of course, for other effects.

Thus, cosmetic compositions containing keratolytic active agents are used for combating ageing, and in particular exfoliant active agents or active agents for promoting cell renewal, such as α-hydroxy acids (in particular, lactic acid, glycolic acid, citric acid), β-hydroxy acids (in particular, salicylic acid, 5-n-octanoylsalicylic acid) and retinoids (in particular, all-trans or 13-cis retinoic acid, retinol). Unfortunately, if these active agents are used in amounts that are too great, they can cause red blotches on the skin and their use may therefore have to be limited.

Preserving agents, surfactants, fragrances, solvents or propellants may also be involved.

The presence of a substance P antagonist in the form of the combination of niacinamide and of the tyrosine-arginine dipeptide and/or derivatives thereof, in a composition comprising a product liable to exhibit an irritant effect, makes it possible to greatly reduce, or even eliminate, this irritant effect.

This also makes it possible to increase the amount of active ingredient liable to exhibit an irritant effect, compared with the amount of active ingredient normally used, with a view to improved effectiveness.

The use of a substance P antagonist makes it possible, in particular, to multiply by 2-fold to 10-fold or more the amount of active ingredient with an irritant effect, compared with the prior art, by reducing all or some of the discomforts mentioned above.

Irrespective of whether their use is part of the cosmetics or therapeutic field, the compositions according to the invention can be administered orally, enterally or else topically; topical administration will be preferred.

In the case of oral administration, the compositions according to the invention can be in any suitable form, such as an oral solution, gelatine capsules, dragees, soft or hard capsules, tablets to be swallowed or to be chewed, granules to be dissolved, syrup, a solid or liquid food product, etc.

According to the invention, the term "physiologically acceptable medium" is intended to mean a medium that is compatible with the skin, the mucous membranes and/or the scalp and its integuments.

The composition according to the invention may be in any form, including the pharmaceutical forms conventionally used for topical application, and in particular in the form of dispersions of the lotion or serum type, emulsions having a liquid or semi-liquid consistency of the milk type, obtained by dispersion of a fatty phase in an aqueous phase (O/W or inversely (W/O), or suspensions or emulsions having a soft, semi-solid or solid consistency of the cream or gel type, or else multiple emulsions (W/O/W or O/W/O), microemulsions, nanoemulsions, vesicular dispersions of ionic and/or nonionic type, or wax-aqueous phase dispersions. These compositions are prepared according to the usual methods. It may also be in the form of a transdermal system for active or passive release of the active agent(s) by transdermal effect, for example of the patch or gel patch (hydrogel) type.

When the composition is in the form of an emulsion, the proportion of the oily phase of the emulsion can range, for example, from 5% to 80% by weight, and preferably from 5% to 50% by weight, relative to the total weight of the composition. The oils, the emulsifiers and the co-emulsifiers used in the composition in the form of an emulsion are chosen from those conventionally used in the cosmetics or dermatological field. The compositions in the form of an emulsion may be free of emulsifier; when the composition comprises an emulsifier and/or co-emulsifier, the latter are generally present in the composition in a proportion ranging from 0.3% to 30% by weight, and preferably from 0.5% to 20% by weight, relative to the total weight of the composition.

The composition of the invention may thus constitute a composition for treating or caring for the skin (including the scalp), keratin fibres (hair, eyelashes, eyebrows), nails or lips, or an antisun or artificial tanning composition, or else a product for cleansing or removing makeup from the skin, the hair, the eyebrows or the eyelashes, a deodorant product or else a fragrancing compound. It is thus generally preferably colouriess or weakly coloured, and it may optionally contain cosmetic or dermatological active agents. It may then be used as a care base for the skin or the lips (lip balms, protecting the lips against the cold and/or the sun and/or the wind), or as a day or night care cream for the skin of the face and/or of the body. It may also be in the form of a treating or non-treating, colouring or non-colouring shampoo, and of a conditioner.

The composition according to the invention may also constitute a coloured cosmetic composition, and in particular a makeup composition for the skin, the keratin fibres (hair or eyelashes) and/or the mucous membranes, in particular a foundation, a blusher, a rouge or eye shadow, a concealer compound in the form of a stick, a lipstick or a lip gloss, optionally having care or treatment properties. Preferably, it may be a coloured (beige or green) makeup composition for correcting the colour of the complexion.

The invention will be illustrated by the following nonlimiting examples.

EXAMPLE 1

Histological Evaluation of the Average Surface Area of the Capillaries

The tests of Examples 1 and 2 hereinafter were carried out with niacinamide at a final concentration of 0.5% and N-acetyl-tyrosine-arginine-decahexyl ester, provided by the company Sederma, at a final concentration of 0.1%; its chemical structure is as follows:

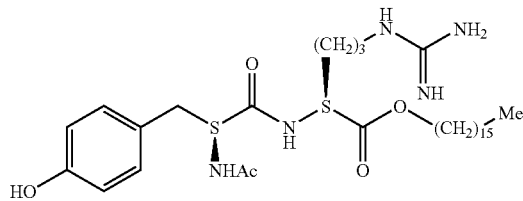

The activity of each of the active agents and of the combination thereof is evaluated in a model of human skin kept under survival conditions. After several hours of re-equilibration of the skin with culture medium (antibiotic+SVF), the culture medium is renewed and substance P at 10 (M, with or without each of the active agents or the combination thereof, is (are) added to the culture medium.

Irrespective of whether they are alone or in combination, the active agents are used at the final concentrations of 0.1% for the niacinamide and 0.5% for the dipeptide.

Morphometric analysis of the surface area ($\mu m^2$) occupied by the lumen of the vessels is carried out by microscopic observation from sections: the skin fragments are fixed in Bouin's solution and embedded in paraffin and then stained with haemalun-eosine. The vascular dilatation is evaluated by counting the number of dilated vessels over the entire histological section (16 fields at 40×magnification).

This analysis makes it possible to determine the average surface area ($\mu m^2$) occupied by the vessels in the dermis.

The treatment with substance P at 10 µM results in a 63% increase in the surface area compared with the normal skin (161.6+/−56.6 µm$^2$ versus 99+/−57.6 µm$^2$ for the normal skin).

| Treatment | Percentage of dilated dermal capillaries |
| --- | --- |
| Control skin | 99 +/− 57.5 |
| Skin + substance P | 161.6 +/− 56.6 |
| Skin + substance P + niacinamide | 108 +/− 27.6 |
| Skin + substance P + dipeptide | 103.16 +/− 34 |
| Skin + substance P + niacinamide + dipeptide | 69.1 +/− 14.8 |

The surface area of the dilated capillaries is significantly decreased, compared with the substance P-treated skin, after application of each of the two active agents (for each, p<0.05).

The combination of the two active agents induces a significant decrease in the average surface area of the capillaries compared with the skin subjected to substance P, but also compared with the control skin.

EXAMPLE 2

Histological Evaluation of Dermal Oedema

Using the sections prepared in Example 1, the oedema is evaluated by means of semi-quantitative scores:
score 0: no oedema
score 1: very slight oedema
score 2: moderate oedema
score 3: considerable oedema The score for the control skin is 0.86+/−0.7. The treatment with substance P results in a 121% increase in the oedema score (1.9+/−0.64).

| Treatment | Percentage of dilated dermal capillaries |
| --- | --- |
| Control skin | 0.86 +/− 0.7 |
| Skin + substance P | 1.9 +/− 0.7 |
| Skin + substance P + niacinamide | 1.03 +/− 0.64 |
| Skin + substance P + dipeptide | 1 +/− 0.6 |
| Skin + substance P + niacinamide + dipeptide | 0.78 +/− 0.3 |

The treatment with each of the active agents makes it possible to significantly decrease the oedema compared with the substance P-stimulated skin (p<0.05). The combination of the two active agents also induces a decrease in the dermal oedema compared with the skin subjected to substance P and compared with the control skin.

For each of these two examples, the application of one or other of the niacinamide and dipeptide active agents makes it possible to bring the parameter measured back to a state corresponding to the control.

The combination of niacinamide and of dipeptide makes it possible, for its part, to significantly decrease the blood vessel dilatation diameter and also results in a decrease in the skin oedema, with a greater activity compared to each of the active agents taken separately.

In conclusion, the effect of the combination of niacinamide and dipeptide is significantly improved compared with the effect of each of the active agents taken separately, and clearly demonstrates the advantages that ensue from the combination of these two active agents.

EXAMPLE 3

Compositions

Oil-in-water Emulsion
A—Water . . . QS 100%
  Preserving agents . . . 0.5%
  Glycerol . . . 5%
  Niacinamide . . . 2.5%
  Dipeptide . . . 2.5%
  Caffeine . . . 0.3%
  Dipeptide . . . 1%
B—Glyceryl stearate and PEG-100 stearate . . . 3%
  Stearic acid . . . 1%
  Cetyl alcohol . . . 2%
  Isononyl isononanoate . . . 10%
  Acrylate copolymer . . . 0.3%

C—Cyclohexasiloxane . . . 5%
Carbomer . . . 0.3%
Xanthan gum . . . 0.2%

Procedure

Phase A is heated at 85° C., with agitation, until a clear phase is obtained and is then brought back to 70° C.

Phase B is heated to 70° C. and homogenized with agitation and then added to phase A for emulsification with agitation. The whole is brought back to 30° C.

The xanthan gum and the carbomer are dispersed in the cyclohexasiloxane at ambient temperature until a homogeneous phase is obtained, and then added to the mixture A+B.

The whole is brought back to ambient temperature. A homogeneous emulsion for treating problems of skin redness is obtained.

Anti-hair Loss Lotion

| Dextran sulphate 500kD | 0.5% |
|---|---|
| Aminexil | 1.5% |
| Salicylic acid | 0.2% |
| Dipeptide | 2% |
| Niacinamide | 3% |
| Propylene glycol | 30% |
| Ethyl alcohol | 40.5% |
| Water | qs 100% |

Peel Composition

| Dextran sulphate 1000kD | 1% |
|---|---|
| Glycolic acid | 10% |
| Lactic acid | 10% |
| Dipeptide | 3% |
| Niacinamide | 2% |
| Calcium-D-pantetheine sulfonate | 1% |
| Water | 15% |
| Ethanol | qs 100% |

Depigmenting Patch:

A gel having the following composition is prepared:

| Vitamin C | 2% |
|---|---|
| Salicylic acid | 0.2% |
| Niacinamide | 4% |
| Dipeptide | 4% |
| Methyl sulphonyl methane | 5% |
| Glycerol | 5% |
| Sodium alginate | 10% |
| Polyvinyl alcohol | 10% |
| Sodium polyacrylate (Aronvis S from NIHON JUNYAKU) | 5% |
| Preserving agents | 1% |
| Water | qs 100% |

After mixing of the components, the gel thus obtained is coated onto a support made of nonwoven and then cut up to form a patch.

The above written description of the invention provides a manner and process of making and using it such that any person skilled in this art is enabled to make and use the same, this enablement being provided in particular for the subject matter of the appended claims, which make up a part of the original description and including the combination of niacinamide and of tyrosine-arginine dipeptide, and/or derivatives thereof, particularly the synergistic combination of niacinamide and of tyrosine-arginine dipeptide, and/or derivatives thereof, and uses thereof for preventing and/or decreasing red blotches on the skin and/or puffiness of the skin.

As used herein, the phrases "selected from the group consisting of," "chosen from," and the like include mixtures of the specified materials. Terms such as "contain(s)" and the like as used herein are open terms meaning 'including at least' unless otherwise specifically noted.

As used herein, the phrase "one or more tyrosine-arginine dipeptide compounds" means one or more of tyrosine-arginine dipeptide and a derivative thereof, said derivatives being described above and including protected forms, for instance acylation or acetylation of the amino-terminal end or amidation of the carboxy-terminal end, the N-acetyl-tyrosine-arginine-O-hexadecyl ester, and modified forms described in WO 98/07744.

Amounts listed herein are by weight unless otherwise noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention method and composition is preferably used by subjects desirous of the benefits noted herein, subjects "in need of" these benefits. Such subjects are typically suffering from disorders associated with an excess synthesis and/or release of substance P, such as by self diagnosis or cosmetician or medical diagnosis, or are at recognized and appreciated risk of developing such conditions and who use the invention methods and compositions to combat these effects.

Naturally, one using the invention as disclosed will use an amount of the invention combination effective to reduce the severity of, or treat, disorders associated with an excess synthesis and/or release of substance P. Such amount is inclusive of an amount of the compositions described herein at the disclosed concentrations of active ingredients sufficient to cover the area of the skin being treated in a single application, and of course includes that amount applied upon repeated application, for example on a daily basis over a course of days, weeks, etc. In a preferred embodiment the invention process includes multiple applications of the invention composition to the area(s) of skin in need of attention.

The invention claimed is:

1. A process for the treatment of skin, scalp and/or mucous membrane disorders associated with an excess synthesis and/or release of substance P, comprising applying to skin, scalp and/or mucous membrane in need thereof a substance P antagonist effective amount of a composition comprising a 0.01-20 wt. % of niacinamide, based on a total weight of the composition, and 0.001-20 wt. % of one or more tyrosine-arginine dipeptide compounds, based on a total weight of the composition with the proviso that the composition does not comprise glutathione.

2. The process according to claim 1, for reducing the intensity of red blotches on the skin, lightening skin complexion, making skin complexion uniform, masking surface red blotches on the skin, and/or fading out noticeable microcirculation.

3. The process according to claim 1, for preventing a puffy appearance of the skin, making the figure, the neck and/or the oval of the face more slender, decreasing bags under the eyes, and/or treating puffy ankles and/or legs.

4. The process according to claim 1, wherein the composition comprises N-acetyl-tyrosine-arginine-O-hexadecyl ester.

5. The process according to claim 1, wherein the composition comprises 0.01-10 wt. % of one or more tyrosine-arginine dipeptide compounds, based on a total weight of the composition.

6. The process according to claim 5, wherein the composition comprises 0.1-10 wt. % of niacinamide, based on a total weight of the composition.

7. The process according to claim 1, wherein the composition further comprises a calmative chosen from extracts of rose, bisabolol, D-panthenol, allantoin, madecassoside, extracts of *Centella asiatica*, potassium glycyrrhizinate, caffeine and mixtures thereof.

8. The process according to claim 1, wherein the composition comprises a red blotch decreasing and skin puffiness decreasing combination of niacinamide and one or more tyrosine-arginine dipeptide compounds.

9. The process according to claim 8, wherein the composition comprises N-acetyl-tyrosine-arginine-O-hexadecyl ester.

10. The process according to claim 8, wherein the composition comprises at least one dipeptide compound corresponding to the following general formula:

R1-L-Tyr-L-Arg-R2 wherein:
R1 is a hydrogen atom or an —R3-C=O group and R3 is an optionally hydroxylated, saturated or unsaturated, linear or branched alkyl chain containing from 1 to 20 carbon atoms, an aryl group, an arylalkyl group, an alkyloxy group or an arylalkyloxy group, and
R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

11. The process according to claim 1, wherein the composition comprises at least one dipeptide compound corresponding to the following general formula:

R1-L-Tyr-L-Arg-R2 wherein:
R1 is a hydrogen atom or an —R3-C=O group and R3 is an optionally hydroxylated, saturated or unsaturated, linear or branched alkyl chain containing from 1 to 20 carbon atoms, an aryl group, an arylalkyl group, an alkyloxy group or an arylalkyloxy group, and
R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

12. A composition comprising a combination of 0.01-20 wt. % of niacinamide, based on a total weight of the composition, and 0.001-20 wt. % of one or more tyrosine-arginine dipeptide compounds, based on a total weight of the composition, wherein the composition is effective for the treatment of one or more skin, scalp or mucous membrane disorders associated with an excess synthesis and/or release of substance P, and wherein the combination of niacinamide and one or more tyrosine-arginine dipeptide compounds imparts a substance P antagonist activity to the composition with the proviso that the composition does not comprise glutathione.

13. The composition according to claim 12, wherein the composition comprises 0.1-10 wt. % of niacinamide, based on a total weight of the composition.

14. The composition according to claim 13, wherein the composition comprises 0.01-10 wt. % of one or more tyrosine-arginine dipeptide compounds, based on a total weight of the composition.

15. The composition according to claim 12, wherein the composition comprises at least one dipeptide compound corresponding to the following general formula:

R1-L-Tyr-L-Arg-R2 wherein:
R1 is a hydrogen atom or an —R3-C=O group and R3 is an optionally hydroxylated, saturated or unsaturated, linear or branched alkyl chain containing from 1 to 20 carbon atoms, an aryl group, an arylalkyl group, an alkyloxy group or an arylalkyloxy group, and
R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

16. The composition according to claim 12, wherein the composition comprises N-acetyl-tyrosine-arginine-O-hexadecyl ester.

17. The process according to claim 8, wherein the composition comprises 0.1-10 wt. % of niacinamide, based on a total weight of the composition.

18. The process according to claim 17, wherein the composition comprises 0.01-10 wt. % of one or more tyrosine-arginine dipeptide compounds, based on a total weight of the composition.

19. The process according to claim 1, for preventing red blotches on the skin.

20. The process according to claim 1, for treating red blotches on the skin.

21. The process according to claim 1, for reducing the appearance of blood capillaries in the skin.

22. The process according to claim 19, wherein the composition comprises at least one dipeptide compound corresponding to the following general formula:

R1-L-Tyr-L-Arg-R2 wherein:
R1 is a hydrogen atom or an —R3-C=O group and R3 is an optionally hydroxylated, saturated or unsaturated, linear or branched alkyl chain containing from 1 to 20 carbon atoms, an aryl group, an arylalkyl group, an alkyloxy group or an arylalkyloxy group, and
R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

23. The process according to claim 20, wherein the composition comprises at least one dipeptide compound corresponding to the following general formula:

R1-L-Tyr-L-Arg-R2 wherein:
R1 is a hydrogen atom or an —R3-C=O group and R3 is an optionally hydroxylated, saturated or unsaturated, linear or branched alkyl chain containing from 1 to 20 carbon atoms, an aryl group, an arylalkyl group, an alkyloxy group or an arylalkyloxy group, and R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

24. The process according to claim 21, wherein the composition comprises at least one dipeptide compound corresponding to the following general formula:

R1-L-Tyr-L-Arg-R2 wherein:
R1 is a hydrogen atom or an —R3-C=O group and R3 is an optionally hydroxylated, saturated or unsaturated, linear or branched alkyl chain containing from 1 to 20 carbon atoms, an aryl group, an arylalkyl group, an alkyloxy group or an arylalkyloxy group, and
R2 is a hydroxyl function; an —O—R4 group with R4 being an alkyl chain containing from 1 to 20 carbon atoms; or an —NH2 or —NHX group with X being an alkyl chain containing from 1 to 4 carbon atoms.

25. The process according to claim 19, wherein the dipeptide compound is N-acetyl-tyrosine-arginine-O-hexadecyl ester.

26. The process according to claim 20, wherein the dipeptide compound is N-acetyl-tyrosine-arginine-O-hexadecyl ester.

27. The process according to claim 21, wherein the dipeptide compound is N-acetyl-tyrosine-arginine-O-hexadecyl ester.

28. A process for inhibiting puffiness around the eyes comprising applying to skin around the eyes in need thereof a substance P antagonist effective amount of a composition comprising a 0.01-20 wt. % of niacinamide, based on a total weight of the composition, and 0.001-20 wt. % of one or more tyrosine-arginine dipeptide compounds, based on a total weight of the composition in an amount sufficient to inhibit puffiness around the eyes with the proviso that the composition does not comprise glutathione.

29. The process according to claim 1, wherein the composition comprises 0.01-10 wt. % of N-acetyl-tyrosine-arginine-O-hexadecyl ester and 0.1-10 wt. % of niacinamide.

30. The composition according to claim 12, which comprises 0.01-10 wt. % of N-acetyl-tyrosine-arginine-O-hexadecyl ester and 0.1-10 wt. % of niacinamide.

31. The process according to claim 28, wherein the composition comprises 0.01-10 wt. % of N-acetyl-tyrosine-arginine-O-hexadecyl ester and 0.1-10 wt. % of niacinamide.

* * * * *